United States Patent [19]

Kasai et al.

[11] Patent Number: 5,112,712

[45] Date of Patent: May 12, 1992

[54] ELECTROPHOTOGRAPHIC PHOTOSENSITIVE MATERIALS COMPRISING AN INORGANIC PHOTOCONDUCTOR AND N-HYDROXYIMIDE COMPOUNDS

[75] Inventors: Seishi Kasai; Kazuo Ishii; Eiichi Kato, all of Shizuoka, Japan

[73] Assignee: Fuji Photo Film Co., Ltd., Kanagawa, Japan

[21] Appl. No.: 600,047

[22] Filed: Oct. 19, 1990

[30] Foreign Application Priority Data

Oct. 20, 1989 [JP] Japan .................................. 1-274440

[51] Int. Cl.$^5$ .............................................. G03G 5/087
[52] U.S. Cl. ...................................... 430/95; 430/87; 430/96
[58] Field of Search ............................. 430/95, 87, 96

[56] References Cited

U.S. PATENT DOCUMENTS 4,910,112 3/1990 Kato et al. .............................. 430/96
4,957,988 9/1990 Irving et al. ........................ 430/325

*Primary Examiner*—Marion E. McCamish
*Assistant Examiner*—S. Rosasco
*Attorney, Agent, or Firm*—Sughrue, Mion, Zinn, Macpeak & Seas

[57] ABSTRACT

This invention provides an electrophotographic photosensitive material comprising a conductive support having thereon a photoconductive layer containing at least an inorganic photoconductor and a binder resin, wherein the photoconductive layer contains an N-hydroxyimide compound represented by the following general formula (I):

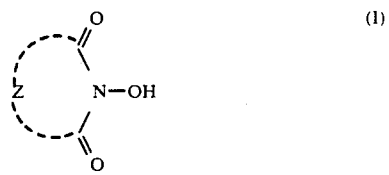

wherein Z represents an organic residue capable of forming a cyclic compound having a saturated or unsaturated bond, thereby increasing its photosensitivity and improving its chargeability, dark charge retentivity and photosensitivity over a wide range from visible to infrared regions. Upon actual reproduction, the inventive material provides a fog-free and clear image even under severe conditions such as hightemperature and high humidity conditions (e.g., 30° C. and 80% RH).

4 Claims, No Drawings

ELECTROPHOTOGRAPHIC PHOTOSENSITIVE MATERIALS COMPRISING AN INORGANIC PHOTOCONDUCTOR AND N-HYDROXYIMIDE COMPOUNDS

FIELD OF THE INVENTION

The present invention relates to an electrophotographic photosensitive material and, more particularly, to an electrophotographic photosensitive material which is much improved in photosensitivity and so is best-suited for CPC, PPC and other purposes.

BACK GROUND OF THE INVENTION

In general, a photosensitive material composed mainly of inorganic photoconductive powders in a finely divided form has been prepared by dispersing the powders in a binder resin and coating the dispersion on supports such as paper or plastic supports to which conductivity is imparted. The thus prepared resin dispersion type of photosensitive material has had wide applications because of the inorganic photoconductor having generally a high sensitivity—the rate of decay of the charged potential of the photosensitive material by light and showing a reduced or limited dark decay of charges—charge leakage in the dark. In order to make the sensitivity of such photosensitive materials higher than so far achieved, various sensitizing dyes are added, as is the case with silver salt photography. Problems associated with such sensitizing dyes, however, are that their quality deteriorates esp. when they are used as photosensitive materials for CPC, since they have to be added in amounts so large that they give rise to a serious coloration of photoconductive layers that are the surface layers of photosensitive materials.

In order to solve such problems, some efforts have been made about how inorganic photoconductors are sensitized. For instance, Japanese Patent Kokai Publication No. 51(1986)-124933 discloses that an improved sensitizing effect is obtained by using as a sensitizer for zinc oxide an acylhydrazone, triazole, imidazolone, imidathion or benzimidazole derivative and an acid anhydride such as those set forth in, e.g., Kokado and Nakayama et al., "Electrophotography", 12, page 20 (1972) in place of, or in combination with, a sensitizing dye.

However, photosensitive materials to which such compounds are added are seriously degraded in terms of dark decay characteristics, although having an improved photosensitivity, and so are practically less than satisfactory in terms of electrophotographic characteristics.

SUMMARY OF THE INVENTION

An object of the present invention is to provide an electrophotographic photosensitive material having an improved photosensitivity without degradation of dark decay characteristics.

Other objects of the present invention will become apparent from the following description and examples.

As a result of intensive and extensive studies made to provide a solution to such problems as referred to above, the inventors have found that an improved sensitizing effect upon increasing photosensitivity with no degradation of dark decay characteristics is achieved by adding an N-hydroxyimide compound as a sensitizer for inorganic photoconductors. This finding underlies the present invention.

More specifically, the present invention provides an electrophotographic photosensitive material comprising a conductive support having thereon a photoconductive layer containing at least an inorganic photoconductor and a binder resin, characterized in that the photoconductive layer contains an N-hydroxyimide compound represented by the following general formula (I):

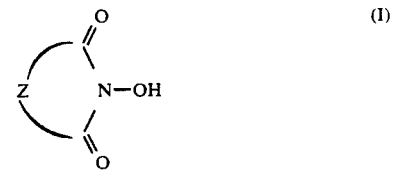

wherein Z represents an organic residue capable of forming a cyclic compound having a saturated or unsaturated bond.

DETAILED DESCRIPTION OF THE INVENTION

Owing to containing the N-hydroxyimide compound represented by the general formula (I), the electrophotographic photosensitive material according to this invention has an increased effective carrier life, probably because holes of electron-hole pairs occurring in the photoconductor by exposure to light are so trapped and localized by the N-hydroxyimide compound that their probability of recombination with electrons is reduced or limited. This can in turn make a contribution to improvements in photosensitivity, chargeability and dark charge retentivity, in particular, photosensitivity over an wide range from visible to infrared regions. Actually reproduced images are fog-free and clear under severe conditions such as hightemperature and high humidity conditions (e.g., 30° C. and 80% RH).

The N-hydroxyimide compounds contained in the electrophotographic photosensitive materials according to the present invention are preferably represented by the following general formula (II):

wherein:

z represents a hydrocarbon chain which has 2 to 5 carbon atoms or in which at least one of the carbon atoms is substituted with a nitrogen atom and/or an oxygen atom, (i) A and B, which may be linked to the constitutional atoms of z and may be identical with or different from each other, each represents a hydrogen atom; an alkyl group which may be substituted; an aralkyl group which may be substituted; a cycloalkyl group which may be substituted; an aryl group which may be substituted; a halogen atom; a cyano group; a nitro group; a hydroxyl group; a group —OR$_1$; a group —SR$_1$; or

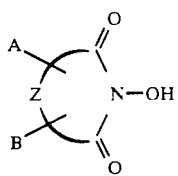

(II)

in which $R_1$, $R_2$ and $R_3$ each represent a hydrogen atom; an alkyl group which may be substituted; an aralkyl group which may be substituted; a cycloalkyl group which may be substituted; or an aryl group which may be substituted; or $R_2$ and $R_3$ may be linked together to form a 4 to 6 membered heterocyclic ring containing at least one hetero-atom, or alternatively, A and B represent:

(ii) a group capable of forming an aliphatic ring which may be substituted together with the constitutional atoms of z;

(iii) a group capable of forming an aromatic ring which may be substituted together with the constitutional atoms of z; or (iv) a group capable of forming a heterocyclic ring which may be substituted together with the constitutional atoms of z.

Referring more illustratively to A and B in the general formula (II), (i) the alkyl groups which may be substituted should preferably have 1-18 carbon atoms in their alkyl moieties. For instance, mention is made of methyl, ethyl, propyl, butyl, pentyl, hexyl, octyl, decyl, dodecyl, tridecyl and tetradecyl groups.

The aralkyl groups which may be substituted should preferably have 7-12 carbon atoms in their aralkyl moieties. For instance, mention is made of benzyl, phenetyl, naphthylmethyl and 2-naphthylethyl groups.

The cycloalkyl groups which may be substituted should preferably be 5-8 membered cycloalkyl groups, for instance, cyclobutyl, cyclopentyl and cyclohexyl groups.

The aryl groups which may be substituted, for instance, include phenyl and naphthyl groups.

The halogen atoms, for instance, include fluorine, chlorine, bromine and iodine.

Additional mention is made of cyano, nitro and hydroxyl groups.

If A and B each stand for groups —OR1, —SR1 or

then $R_1$ represents an aliphatic or aryl group. More illustratively, $R_1$ may be the same aliphatic or aryl groups as referred to above. $R_2$ and $R_3$, which may be identical with or different from each other, each represent a hydrogen atom or a hydrocarbon group. More illustratively, the hydrocarbon group may be the same aliphatic or aryl groups as referred to above. Alternatively, $R_2$ and $R_3$ may be linked together to form a 4-6 membered heterocyclic ring group containing at least one hetero-atom. The heterocyclic ring group, for instance, may be pyrrodinyl, pyrrolinyl, piperidyl, piperazinyl, indolinyl, morpholinyl and quinuclidinyl groups.

(ii) The aliphatic rings, which A and B may form together with the constitutional atoms of z and which may be substituted, may contain an unsaturated bond therein and should preferably have 3-14 carbon atoms in their ring skeletons.

These aliphatic rings, for instance, include rings such as cyclobutane, cyclopentane, cyclopentanone, cyclopentene cyclohexane, cyclohexanone, cyclohexene, cyclohexadiene, cycloheptane, cycloheptene, cycloheptadiene, cycloheptatriene, cycloheptanone, cyclooctane, cyclooctene, cyclooctatriene, bicyclopentane, bicyclohexane, bicyclohexene, norcarane, norbornane, norbornene, norbornadiene, decalin and hydroazulene rings.

(iii) The aromatic rings, which A and B may form with the constitutional atoms of z and which may be substituted, include benzene, naphthalene, anthracene and phenanthrene rings, by way of example alone.

(iv) The heterocyclic rings, which A and B may form together with the consitutional atoms of z and which may be substituted, include rings such as imidazolidine, pyrrolidine, hydrofuran, oxazolidine, piperidine, piperazine, pyridine, hydropyran, pyran, pyrrole, thiophene, N-hydroxyphthalimide, N-hydroxy-4,5-cyclohexanedicarboxyimide and N-hydroxy-6,7-naphthodicarboxyimide rings, Of the N-hydroxyphthalimide compounds used in this invention, those represented by the following general formulae (III)-(VI) are particularly preferred.

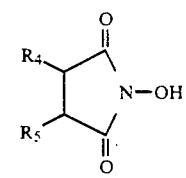

(III)

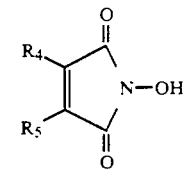

(IV)

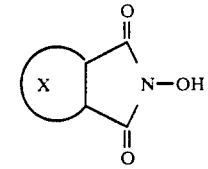

(V)

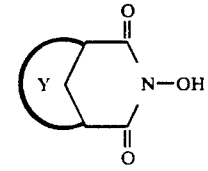

(VI)

In the general formula (III), substituents $R_4$ and $R_5$ may be identical with or different from each other. Preferable examples of such substituents $R_4$ and $R_5$ as well as $R_4$ and $R_5$ in the general formula (IV) are:

a hydrogen atom or groups such as methyl, ethyl, 2-methoxyethyl, 2-ethoxyethyl, 2-hydroxyethyl, 2-chloroethyl, 2-cyanoethyl, 2-(N,N-dimethylamino)ethyl, n-propyl, isopropyl, 3-hydroxypropyl, 2-hydroxypropyl, 2,3-dihydroxypropyl, 3-carbamoylpropyl, n-butyl, t-butyl and n-hexyl groups;

atoms such as fluorine, chlorine, bromine and iodine or groups such as cyano, nitro and hydroxy groups;

groups such as benzyl, methoxybenzyl, ethoxybenzyl, methybenzyl, dimethylbenzyl, chlorobenzyl, dichlorobenzyl, dibromobenzyl, acetoxybenzyl, cyanobenzyl, nitrobenzyl and chlorobenzyl; and groups such as phenyl, tolyl, xylyl, mesityl, methoxyphenyl, ethoxyphenyl, p-chlorophenyl, dichlorophenyl, bromophenyl, dibromophenyl, chlorobromophenyl, chloromethylphenyl, bromomethyl-phenyl, acetoxyphenyl, acetylphenyl, methoxycarbonylphenyl, aminophenyl, dimethylaminophenyl, dimethylaminophenyl, diethylaminophenyl, cyanophenyl and nitrophenyl groups.

It is noted that the above-mentioned aromatic rings may be substituted by the substituents at any one of the o, m and p-positions.

Preferable examples of the rings represented by X in the foregoing general formula (V) are:

cyclobutane, cyclopentane, 4-methylcyclopentane, 4-chlorocyclopentane, cyclopentene, cyclohexane, 4-hydroxycyclohexane, 4-methylcyclohexane, 4,5-dimethylcyclohexane, 4-chlorocyclohexane, 4,5-dichlorocyclohexane, 4-cyanocyclohexane, cyclohexene, 4-methylcyclohexene, 4-chlorocyclohexene, cycloheptane, 4,5,6-trichlorocycloheptane, 5,5-dichlorocycloheptane, cycloheptene, norbornane, 6,7-dichloronorbornane, 1-chloronorbornane, 1-methylnorbornane, 1-methoxynorbornane, 1-chloronorbornene, 1-methoxylnorbornene, bicylohexane and 5-chlorobicyclohexane rings;

aromatic rings such as benzene, 4-methoxybenzene, 4-methylbenzene, 4-N,N-dimethylaminobenzene, 4-N,N-diethylaminobenzene, 4-aminobenzene, 4-hydroxybenzene, 4-chlorobenzene, 4-cyano-benzene, 4-nitrobenzene, 3,5-dimethoxybenzene, 3,5-dichlorobenzene, 3,5-dinitrobenzene, 1,2-naphthalene, 1,8-naphthalene, 2,3-naphthalene, 3-chloro-1,2-naphthalene, 6-chloro-1,2-naphthalene, 3-methoxy-1,2-naphthalene, 6-methoxy-1,2-naphthalene, 8-nitro-2,3-napthalene, 4-nitro-1,8-naphthalene, 4,5-dinitro-1,8-naphthalene, 1,2-anthracene and 2,3-anthracene rings; and heterocyclic rings such as pyridine, 6-methylpyridine, 6-chloropyridine, 2-methylpyridine, 2-chloropyridine, 4-methylpyridine, 2-methylpyrrolidine, N-methlpiperidine, 4-chloropiperidine, N,N-dimethylpiperazine, N-hydroxyphthalimide, N-hydroxy-4,5-cyclohexanedicarboxyimide, N-hydroxy-2,3-napthodicarboxyimide and N-hydroxy-6,7-naphthodicarboxyimide.

Preferable examples of the rings represented by Y in the above-mentioned general formula (VI) are aromatic rings such as 1,8-naphthalene, 1,9-anthracene and 1,9-phenathrene.

In addition to the compounds represented by the general formulae (III)–(VI), the following compounds (48)–(54), (74), (103) and (104) may be used.

Set out below are more illustrative examples of the N-hydroxyimide compounds used in this invention; however, the scope of the invention is never limited thereto.

(1) [structure]

-continued (2) [structure with OCH₃]

(3) [structure with H₃CO and OCH₃]

(4) [structure with Cl]

(5) [structure with Cl, Cl]

(6) [structure with NO₂]

(7) [structure with O₂N and NO₂]

(8) [structure with CN]

(9) [structure with NC and CN]

(10) [structure with N(CH₃)₂]

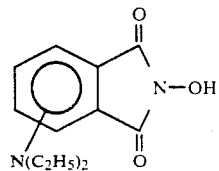
(11)
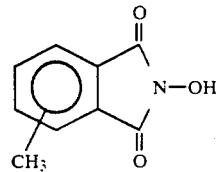
(12)
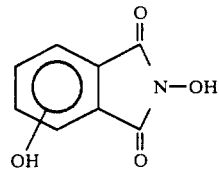
(13)
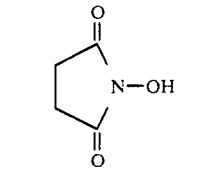
(14)
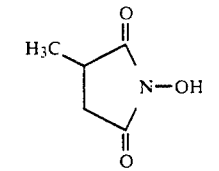
(15)
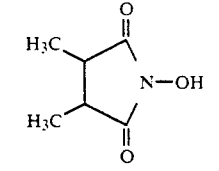
(16)
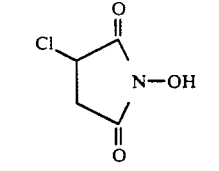
(17)
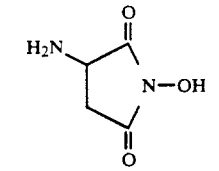
(18)
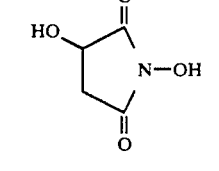
(19)
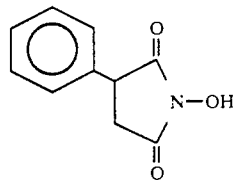
(20)
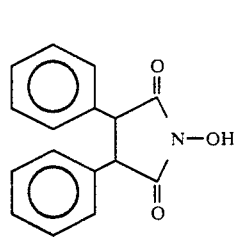
(21)
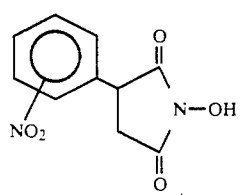
(22)
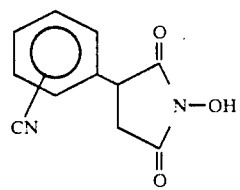
(23)
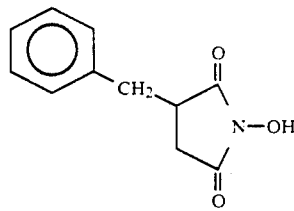
(24)
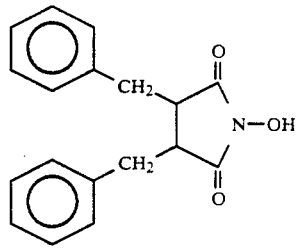
(25)
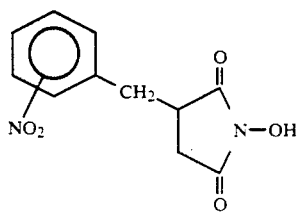
(26)

-continued
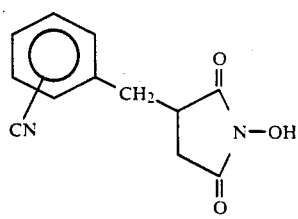
(27)
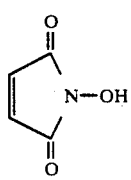
(28)
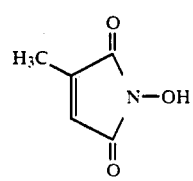
(29)
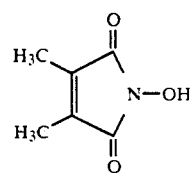
(30)
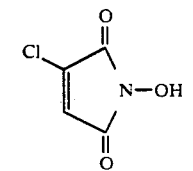
(31)
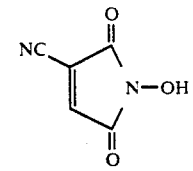
(32)
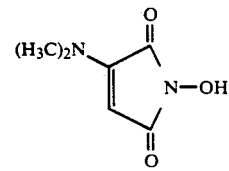
(33)
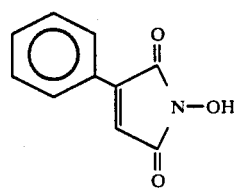
(34)
-continued
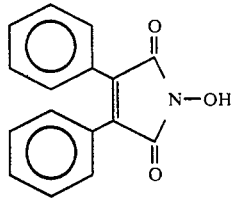
(35)
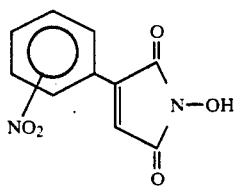
(36)
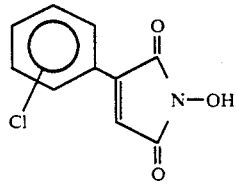
(37)
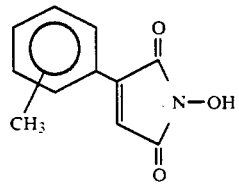
(38)
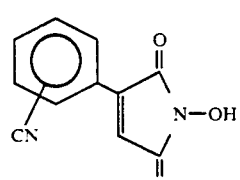
(39)
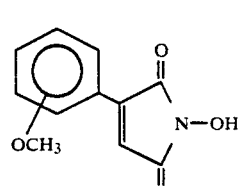
(40)
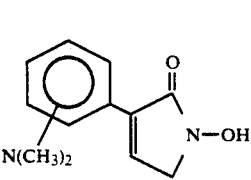
(41)
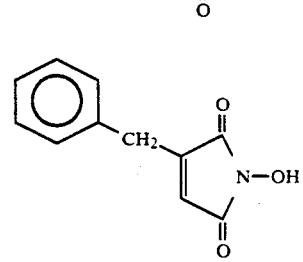
(42)

-continued
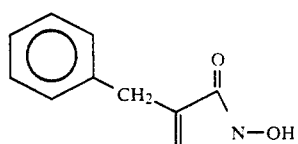 (43)
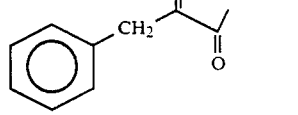 (44)
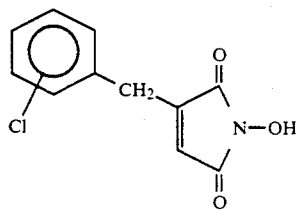 (45)
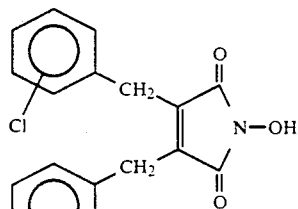 (46)
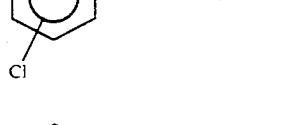 (47)
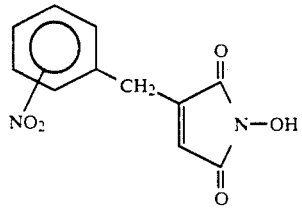 
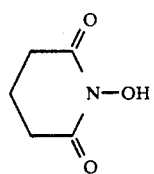 (48)
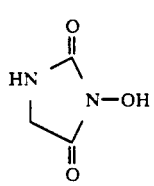 (49)
-continued
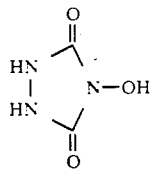 (50)
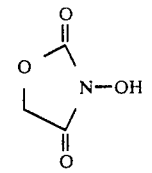 (51)
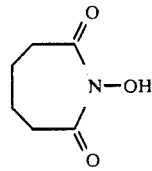 (52)
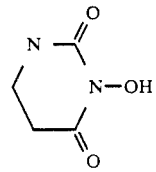 (53)
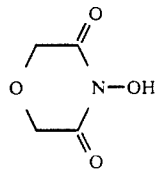 (54)
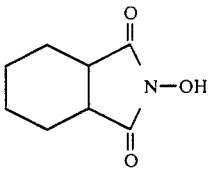 (55)
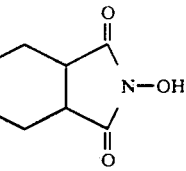 (56)
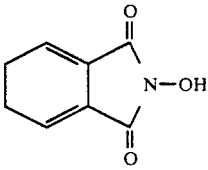 (57)
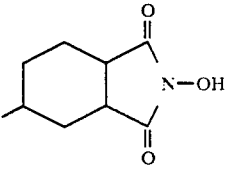 (58)

-continued
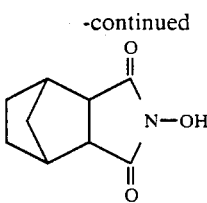 (59)
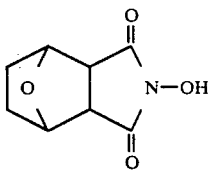 (60)
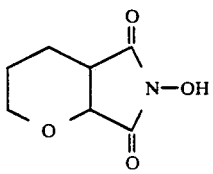 (61)
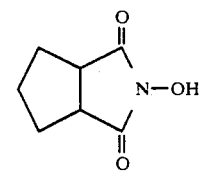 (62)
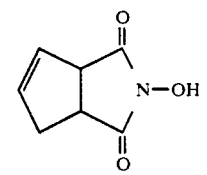 (63)
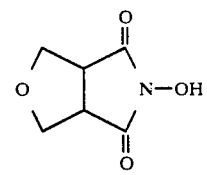 (64)
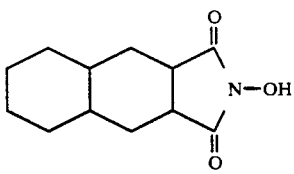 (65)
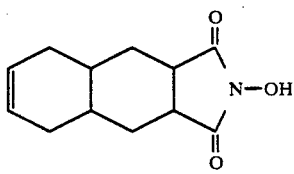 (66)
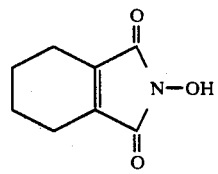 (67)
-continued
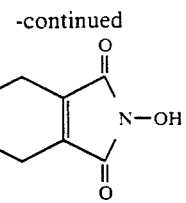 (68)
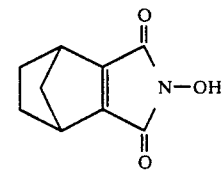 (69)
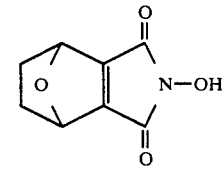 (70)
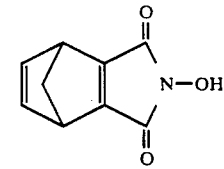 (71)
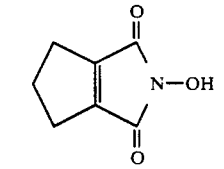 (72)
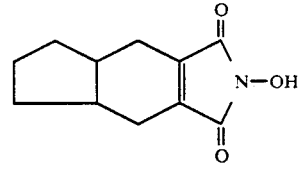 (73)
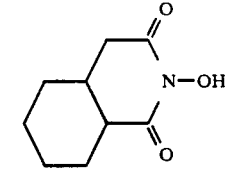 (74)
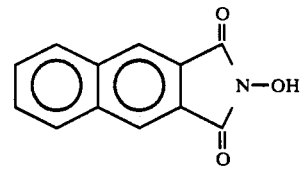 (75)
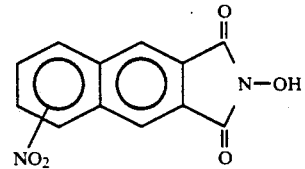 (76)

-continued
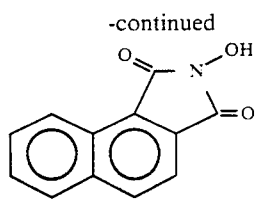 (77)
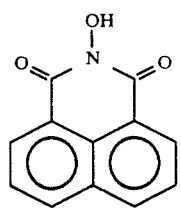 (78)
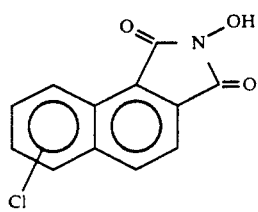 (79)
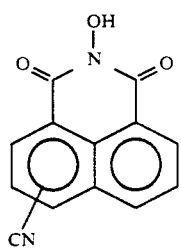 (80)
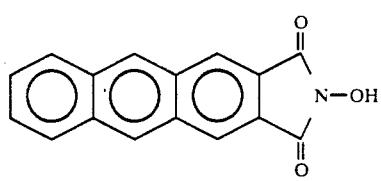 (81)
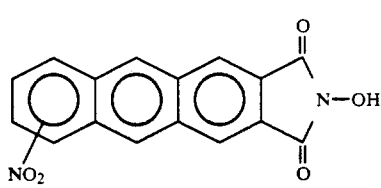 (82)
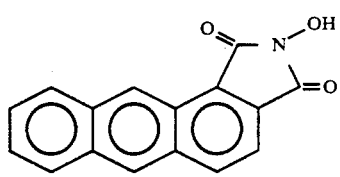 (83)
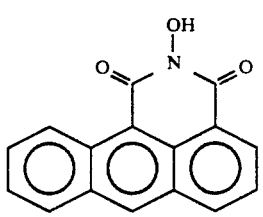 (84)
-continued
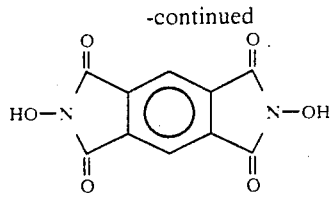 (85)
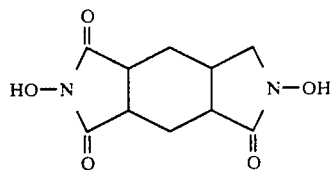 (86)
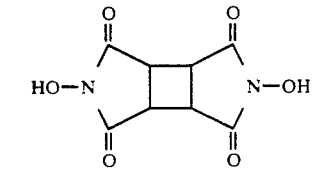 (87)
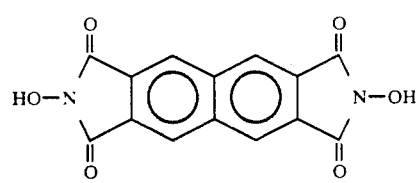 (88)
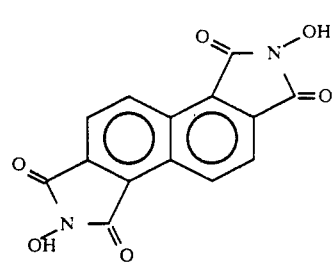 (89)
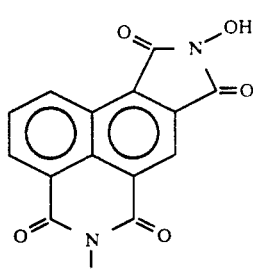 (90)
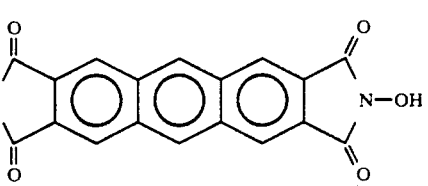 (91)
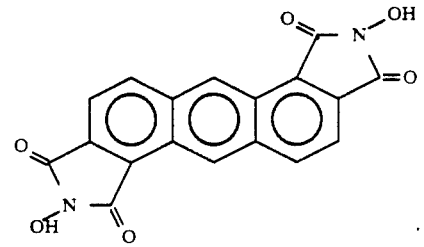 (92)

(93) 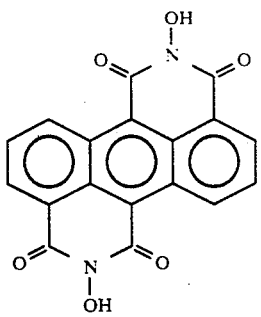

(94) 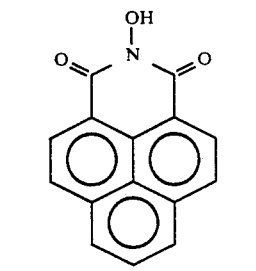

(95) 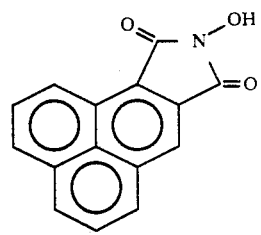

(96) 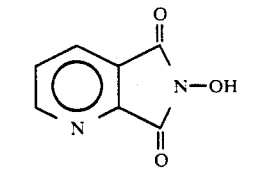

(97) 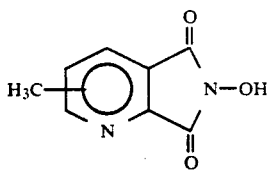

(98) 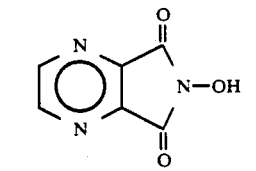

(99) 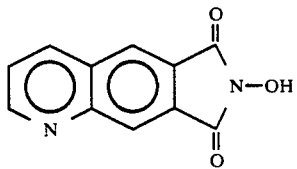

(100) 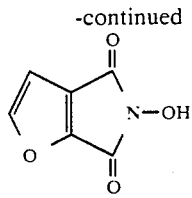

(101) 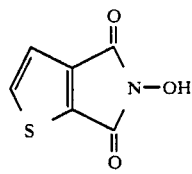

(102) 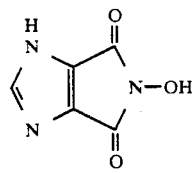

(103) 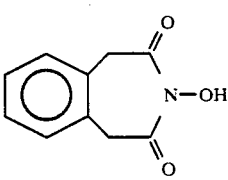

(104) 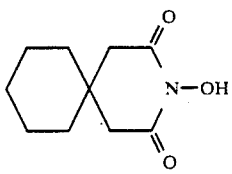

The N-hydroxyimide compounds according to this invention may be used alone or in combination of two or more. They may also be used in combination with other chemical sensitizers as well. The N-hydroxyimide compounds used in this invention may be synthesized according to the methods set forth in:

G. F. Jaubert, "Ber.", 28, 360 (1859),

D. E. Ames et al, "J. Chem. Soc.", 3518 (1955), and

M. A. Stolberg et al, "J. Amer. Chem. Soc.", 79, 2615 (1957).

The inorganic photoconductors used in this invention, for instance, include zinc oxide, titanium oxide, zinc sulfide, cadmium sulfide, cadmium carbonate, zinc selenide, cadmium selenide, tellurium selenide and lead sulfide. However, preference is given to zinc oxide and titanium oxide.

As the binder resins used in this invention, use may be made of all resins known in the art. Typical resins are copolymers of vinyl chloride/vinyl acetate, styrene/vinyl butadiene and styrene/butyl methacrylate; polymethacrylate; polyacrylate; polyvinyl acetate; polyvinylbutyral; alkyd resin; silicone resin; epoxy resin; epoxy ester resin; and polyester resin. These may be used in combination with an aqueous acryl ester emulsion. Examples of specific polymeric materials useful as the binder resins are set forth in "Research Disclosure", Vol. 109, pp. 61-67 under the title "Electrophotographic Elements, Materials and Processes".

The amount of the N-hydroxyimide compound incorporated in the photosensitive layer is suitably in the range of 0.001 to 10 parts by weight, preferably 0.01 to 2 parts by weight per 100 parts by weight of photoconductor.

If the amount of the N-hydroxyimide compound is less than 0.001 part by weight, the sensitizing effect may not be sufficient. On the other hand, when the amount exceeds 10 parts by weight, an extent of the increase in sensitivity becomes small.

It has been found that more preferred results are obtained by using the N-hydroxyimide compound according to this invention in combination with a sensitizing dye than by using it by itself.

The sensitizing dyes used to impart a more increased photosensitivity to the photoconductors used in this invention may be those well-known in the photoconductor sensitization art. Typical sensitizing dyes are set forth in:

"Society of Photographic Scientists and Engineers", 19, pp. 60–64 (1975);

"Applied Optics", Suppl. 3, 50 (1969);

U.S. Pat. Nos. 3037861, 3250615 and 3712811;

GB Patent No. 1353264;

"Research Disclosure", 10938 (May 1973), p. 62 ff.;

U.S. Pat. Nos. 3141700 and 3938994;

Japanese Patent Kokai Publication Nos. 56-14560, 56-14561, 56-29586, 56-29587, 56-35141 and 56-65885;

Japanese Patent Application No. 55-114259; and so on.

Examples of polymethine dyes, which provide a spectral sensitization of near to far infrared regions at a long wavelength of 700 nm or above, are described in:

Japanese Patent Kokai Publication Nos. 47-840 and 47-44180;

Japanese Patent Publication No. 51-41061;

Japanese Patent Kokai Publication No. 49-5034, 49-45122, 57-46245, 56-35141, 57-157254, 61-26044, 61-27551, 63-264763, 63-124054 and 63-241561;

U.S. Pat. Nos. 3619154 and 4175956;

"Research Disclosure" 1982, 216, pp. 117–118; and so on.

In accordance with the present invention, these known sensitizing dyes and other dyes capable of increasing the photosensitivity of inorganic photoconductors may be used selectively.

These sensitizing dyes are used in amounts sufficient to sensitize the inorganic photoconductors. Although varying depending upon the types of the photoconductors and sensitizing dyes used, they may be used in the range of about 0.001 to about 100% by weight, preferably about 0.01 to about 30% by weight based on the weight of photoconductor.

The resin can be mixed with the photoconductor in a range of from 5 to 100 parts by weight, preferably from 10 to 40 parts by weight per 100 parts weight of the photoconductor.

The present invention will now be explained more specifically but not exclusively with reference to the examples.

EXAMPLE 1

A mixture of 20 g (solid matter base) of a copolymer of n-butyl methacrylate, methyl methacrylate and methacrylic acid (DIANAL LR-009 made by Mitsubishi Rayon Co., Ltd.), 100 g of zinc oxide, 0.09 g of heptamethinecyanine dye [A], 0.11 g of N-hydroxyphthalimide (Compound 1 of the invention) and 150 g of toluene was dispersed in a ball mill for 2 hours to prepare a photosensitive layer composition. By means of a wire bar coater, the composition was coated in an amount of 18 g/m$^2$ (dry basis) on paper to which electrical conductivity had been added, dried at 110° C. for 1 minute, and allowed to stand at 20° C. and 65% RH for 24 hours, thereby preparing an electrophotographic photosensitive material.

Cyanine Dye [A]

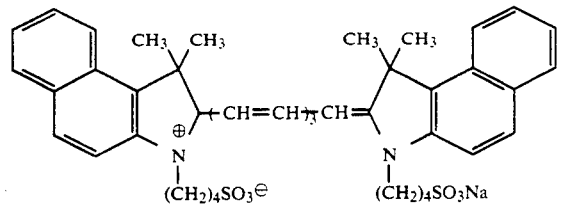

COMPARATIVE EXAMPLE 1

An electrophotographic photosensitive material was prepared by repeating Example 1, provided that N-hydroxyphthalimide was not added.

COMPARATIVE EXAMPLE 2

An electrophotographic photosensitive material was prepared by repeating Example 1, provided that 0.1 g of phthalic anhydride was added in place of N-hydroxyphthalimide.

These photosensitive materials were estimated in terms of electrostatic and imaging characteristics at 20° C. and 65% RH and 30° C. and 80% RH, respectively.

The results are reported in Table 1.

TABLE 1

| | | Ex. 1 | Comp. Ex. 1 | Comp. Ex. 2 |
|---|---|---|---|---|
| Electrostatic characteristics Note: 1 | | | | |
| $V_{10}$ | I (20° C. 65% RH) | 683 | 521 | 560 |
| (V) | II (30° C. 80% RH) | 670 | 480 | 540 |
| D.R.R. | I (20° C. 65% RH) | 88 | 70 | 80 |
| (%) | II (30° C. 80% RH) | 84 | 64 | 75 |
| $B_{1/10}$ | I (20° C. 65% RH) | 30 | 35 | 31 |
| (erg /cm$^2$) | II (30° C. 80% RH) | 33 | 43 | 35 |
| Imaging characteristics Note: 2 | | | | |
| | I (20° C. 65% RH) | ○ good | X Low. DM. Some characters were not reproduced. | △~○ Low. DM |
| | II (30° C. 80% RH) | ○ good | XX Low. DM, Some characters were not reproduced, Remarkable fog | X~△ Low. DM, Fine lines became blurred. |

The electrostatic and imaging characteristics set out in Table 1 were evaluated in the following manners.

(Note 1) Electrostatic Characteristics

Each photosensitive material was negatively charged by corona discharge to a voltage of 6 kV for 20 seconds in a dark room at 20° C. and 65% RH using a paper analyzer ("Paper Analyzer SP-428" made by Kawaguchi Denki Co., Ltd.). After the material had been allowed to stand for 10 seconds, the surface potential $V_{10}$ was measured. Then, the material was kept stationary in the dark for 180 seconds to measure the potential $V_{190}$, thereby finding a charge retention after 180-second dark decay or a dark decay retention (DRR in %) from $(V_{190}/V_{10}) \times 100$ (%).

After negatively charged on the surface of the photoconductive layer by corona discharge, the material was exposed to monochromatic light having a wavelength of 780 nm to measure the length of time during which the surface potential $V_{10}$ decayed to one-tenth, from which an exposure $E_{1/10}$ (erg/cm$^2$) was in turn found.

(Note 2) Imaging Characteristics

For imaging, each photosensitive material was allowed to stand for 24 hours under the same ambient conditions as the following imaging conditions. Then, the material was negatively charged at 5 kV and exposed on the surface to light at an exposure of 64 erg/cm$^2$, a pitch of 25 μm and a scanning speed of 300 m/sec, using as a light source a gallium-aluminium-arsenic semiconductor laser (with an oscillation wavelength of 780 nm), followed by development and fixation using ELP-T (made by Fuji Photo Film Co., Ltd.) as a liquid developer. The resulting reproduced image was visually estimated in terms of fog and image quality. Imaging was carried out under conditions of 20° C. and 65% RH and 30° C. and 80% RH, respectively.

As shown in Table 1, the photosensitive material of this invention was improved in terms of electrostatic characteristics and, upon actual reproduction, provided a fog-free and clear image which was not affected by environmental changes.

In Comparative Example 1 in which Compound (1) is not added to the photosensitive material, there is a serious degradation of electrostatic characteristics (esp., $V_{10}$ and DRR). At the same time, there is a degradation of imaging characteristics for the reasons that the semiconductor laser exposure relies upon a scanning system and imaging characteristics are particularly governed by DRR. Referring to environmental changes, the higher the temperature and humidity, the more likely it is that both the electrostatic (esp., $V_{10}$ and DRR) and imaging characteristics are degraded, or otherwise affected by environmental changes.

Comparative Example 2 in which phthalic anhydride is used for Compound (1) is much more degraded in electrostatic and imaging characteristics than Example 1. Referring to environmental changes, the higher the temperature and humidity, the more likely it is that both the electrostatic and imaging characteristics are degraded, or otherwise affected by environmental changes.

From the foregoing, it is found that Compound (1) of this invention can provide an electrophotographic photosensitive material which meets electrostatic and imaging characteristics alike without being affected by environmental changes.

EXAMPLES 2-6

Example 1 was repeated, provided that the compounds set out in Table 2 were used as the chemical sensitizers according to this invention in place of Compound (1), thereby preparing various electrophotographic photosensitive materials.

TABLE 2

| Ex. | Compounds | Electorstatic Characteristics | | | Imaging Characteristics |
| --- | --- | --- | --- | --- | --- |
| | | $V_{10}$ (—V) | D.R.R (%) | $E_{1/10}$ (erg/cm$^2$) | |
| 2 | (28) | 706 | 87 | 38 | good |
| 3 | (14) | 699 | 90 | 52 | good |
| 4 | (56) | 680 | 88 | 40 | good |
| 5 | (65) | 695 | 86 | 38 | good |
| 6 | (59) | 670 | 87 | 42 | good |

The electrostatic and imaging characteristics were measured at 30° C. and 80% RH.

The photosensitive materials according to this invention were all improved in terms of chargeability, dark charge retentivity and photosensitivity and, upon actual reproduction, produced fog-free and clear images even under severe conditions such as hightemperature and high humidity conditions (e.g.,30° C. and 80% RH).

EXAMPLE 7-9

Example 1 was repeated, provided that the following Dyes (B)-(D) were used in place of Dye (A), thereby preparing various electrophotographic photosensitive materials.

Dye B

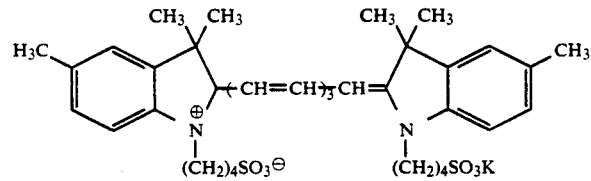

Dye C

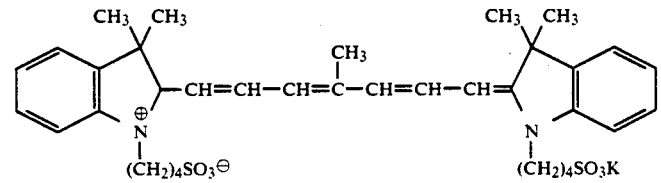

Dye D

-continued

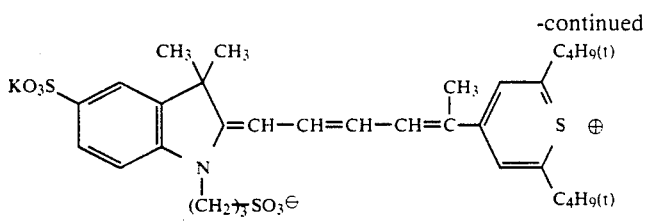

TABLE 3

| Ex. | Dyes for SS* | Electrostatic Characteristics | | | Imaging Characteristics |
|---|---|---|---|---|---|
| | | $V_{10}$ (−V) | D.R.R (%) | $E_{1/10}$ (erg/cm²) | |
| 7 | (B) | 675 | 86 | 26 | good |
| 8 | (C) | 670 | 85 | 27 | good |
| 9 | (D) | 660 | 82 | 30 | good |

SS* Spectral Sensitization

The electrostatic and imaging characteristics were measured at 30° C. and 80% RH.

The chemical sensitizers according to this invention underwent no performance change even when used in combination with various dyes for spectral sensitization, and were all improved in terms of chargeability, dark charge retentivity and photosensitivity. Upon actual reproduction, they provided fog-free and clear images even under severe conditions such as high-temperature and humidity conditions (say, 30° C. and 80% RH).

EXAMPLE 10

Preparation of Resin

A mixed solution of 98% of ethyl methacrylate, 2 g of acrylic acid and 200 g of toluene was heated at a temperature of 70° C. in a nitrogen stream, and 1 g of 2,2'-azobis(2,4-dimethylvaleronitrile) was added to it for a 10-hour reaction. The resulting copolymer had a weight average molecular weight of 33,000 and a glass transition point of 55° C.

Preparation of Photosensitive Material

A mixture of 40 g (solid matter basis) of the above-mentioned resin, 200 g of zinc oxide (Sazex (R)2000 made by Sakai Kagaku Co., Ltd.), 0.2 g of Rose Bengal, 0.02 g of N-hydroxyphthalimide - Compound (1) of this invention and 300 g of toluene was dispersed for 2 hours in a ball mill to prepare a photosensitive layer composition. By means of a wire bar coater, this composition was coated on paper having been made conductive to a dry coverage of 22 g/m², followed by drying at 110° C. for 5 minutes. Then, the paper was allowed to stand in a dark place at 20° C. and 65% RH for 24 hours, thereby preparing an electrophotographic photosensitive material.

COMPARATIVE EXAMPLE 3

Example 10 was repeated, provided that phthalic anhydride was used in place of Compound (1) of this invention, thereby preparing a photosensitive material.

COMPARATIVE EXAMPLE 4

Example 10 was repeated, provided that Compound (1) of this invention was not added, thereby preparing a photosensitive material.

The electrostatic characteristics of these materials were measured at 20° C. and 65% RH and 30° C. and 80% RH, respectively.

The results are reported in Table 4.

TABLE 4

| Electrostatic Characteristics Note 1 | | Ex. 10 | Comp. Ex. 3 | Comp. Ex. 4 |
|---|---|---|---|---|
| $V_0$ | I (at 20° C. and 65% RH) | 752 | 688 | 683 |
| | II (at 30° C. and 80% RH) | 740 | 650 | 620 |
| DRR (%) | I (at 20° C. and 65% RH) | 90 | 80 | 73 |
| | II (at 30° C. and 80% RH) | 88 | 70 | 60 |
| $E_{\frac{1}{2}}$ (lux · sec) | I (at 20° C. and 65% RH) | 14 | 15 | 16 |
| | II (at 30° C. and 80% RH) | 16 | 20 | 22 |

Note 1: Electrostatic Characteristics

Each photosensitive material was charged at 6 kV by corona discharge in a static system, using a paper analyzer ("SP-428 made by Kawaguchi Denki Co., Ltd.), held in a dark place for 20 seconds and exposed to light to estimate its potential characteristics. In other words, a potential $V_0$ just after corona discharge, a retention of $V_{20}$ —a potential after 20 seconds in a dark place—to $V_0$ or a dark decay retention (DRR % = $V_{20}/V_0$) and the exposure required for dark decay of a potential upon negatively charged to 400 V to one half or a half-exposure $E_{1/2}$ (lux/sec) were measured. The light source used gave out white light of 2 lux.

As reported in Table 4, the incorporation of Compound (1) according to this invention makes it possible to obtain an electrophotographic photosensitive material which is more unlikely to be affected by environmental changes than those of Comparative Examples 3 and 4, and has improved electrostatic characteristics.

EXAMPLES 11-22

Example 1 was repeated, provided that the compounds set out in Table 5 were used in place of 0.09 g of Dye (A), 0.1 g of Dye (B) and hydroxyphthalimide, thereby preparing photosensitive materials. The electrophotographic characteristics of such materials, measured in the same manner as in Ex. 1, are reported in Table 5.

TABLE 5

| Examples | Compounds |
|---|---|
| 11 | (4) |
| 12 | (10) |
| 13 | (15) |
| 14 | (20) |
| 15 | (26) |
| 16 | (30) |
| 17 | (48) |
| 18 | (68) |
| 19 | (75) |
| 20 | (78) |
| 21 | (88) |
| 22 | (94) |

The electrostatic and imaging characteristics were measured at 30° C. and 80% RH.

The photosensitive materials of the present invention, into which the compounds according to Examples 11-22 were incorporated, were all improved in terms of chargeability, dark decay retentivity and photosensitivity and, upon actual reproduction, provided fog-free and clear images even under severe conditions such as hightemperature and high humidity conditions (e.g.,30° C. and 80% RH).

While the invention has been described in detail and with reference to specific embodiments thereof, it will be apparent to one skilled in the art that various changes and modifications can be made therein without departing from the spirit and scope thereof.

What we claim:

1. An electrophotographic photosensitive material comprising a conductive support having thereon a photoconductive layer containing at least an inorganic photoconductor and a binder resin, characterized in that the photoconductive layer contains an N-hydroxyimide compound represented by the following general formula (I):

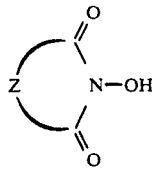

(I)

wherein Z represents an organic residue capable of forming a cyclic compound having a saturated or unsaturated bond.

2. An electrophotographic photosensitive material as claimed in claim 1, wherein the N-hydroxyimide compound is represented by the following general formula (II):

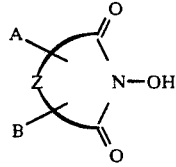

(II)

wherein:
z represents a hydrocarbon chain which has 2 to 5 carbon atoms or a hydrocarbon chain at least one of the carbon atoms is substituted with a nitorgen atom and/or an oxygen atom, (i) A and B, which may be bonded to the constitutional atoms of z and may be identical with or different from each other, each represent a hydrogen atom; an alkyl group which may be substituted; an aralkyl group which may be substituted; a cycloalkyl group which may be substituted; an aryl group which may be substituted; a halogen atom; a cyano group; a nitro group; a hydroxyl group; a group—$OR_1$; a group—$SR_1$; or a group

in which $R_1$, $R_2$ and $R_3$ each represent a hydrogen atom; an alkyl group which may be substituted; an aralkyl group which may be substituted; a cycloalkyl group which may be substituted; or an aryl group which may be substituted; or $R_2$ and $R_3$ may be linked together to form a 4 to 6 membered heterocyclic ring containing at least one heteroatom, or alternatively, A and B represent:
(ii) a group forming an aliphatic ring which may be substituted together with the constitutional atoms of z;
(iii) a group forming an aromatic ring which may be substituted together with the constitutional atoms of z; or
(iv) a group forming a heterocyclic ring which may be substituted together with the constitutional atoms of z.

3. An electrophotographic photosensitive material as claimed in claim 1, wherein an amount of the N-hydroxyimide compound is from 0.01 to 10 parts by weight per 100 parts by weight of the photoconductor in the photoconductive layer.

4. An electrophotographic photosensitive material as claimed in claim 1, wherein the photoconductive layer further contains a sensitizing dye.

* * * * *